United States Patent
Brotherton et al.

(10) Patent No.: US 6,630,672 B1
(45) Date of Patent: Oct. 7, 2003

(54) ON-LINE MEASURING SYSTEM AND METHOD

(75) Inventors: George Alexander Brotherton, Queensland (AU); Stephen Paul Staunton, Queensland (AU); Nils Berding, Queensland (AU); Phillip John Lethbridge, Queensland (AU); Donald Lachlan Mackintosh, Queensland (AU); Philip Gwyther Atherton, Queensland (AU); Scott Clifford Grimley, Queensland (AU)

(73) Assignees: Bureau of Sugar Experiment Stations, Queensland (AU); Sugar North Limited, Queensland (AU)

(*) Notice: Subject to any disclaimer, the term of this patent is extended or adjusted under 35 U.S.C. 154(b) by 0 days.

(21) Appl. No.: 09/581,211
(22) PCT Filed: Nov. 17, 1998
(86) PCT No.: PCT/AU98/00951
§ 371 (c)(1), (2), (4) Date: Jun. 21, 2000
(87) PCT Pub. No.: WO99/34193
PCT Pub. Date: Jul. 8, 1999

(30) Foreign Application Priority Data

Dec. 23, 1997 (AU) .............................................. PP 1155

(51) Int. Cl.⁷ .............................................. G01N 21/35
(52) U.S. Cl. .............................. 250/339.07; 250/338.5; 250/339.12; 250/339.11
(58) Field of Search ........................ 250/339.07, 338.5, 250/339.01, 339.08, 339.09, 339.11, 339.12, 341.8, 339.03

(56) References Cited

U.S. PATENT DOCUMENTS

| | | | | |
|---|---|---|---|---|
| 5,166,755 A | * | 11/1992 | Gat .............................. | 250/226 |
| 5,324,945 A | * | 6/1994 | Iwamoto et al. ........ | 250/339.12 |
| 5,740,073 A | * | 4/1998 | Bages et al. ................. | 700/266 |
| 5,763,883 A | * | 6/1998 | Descales et al. ........ | 250/339.09 |
| 5,898,792 A | * | 4/1999 | Oste et al. ................... | 382/110 |
| 6,002,479 A | * | 12/1999 | Barwicz et al. .............. | 356/326 |
| 6,100,526 A | * | 8/2000 | Mayes .................... | 250/339.11 |
| 6,114,699 A | * | 9/2000 | Barton et al. ........... | 250/339.09 |
| 6,420,708 B2 | * | 7/2002 | Wilks, Jr. et al. ........ | 250/339.07 |

FOREIGN PATENT DOCUMENTS

| | | |
|---|---|---|
| DE | 43 40 505 C 1 | 2/1995 |
| EP | 0 365 205 A2 | 4/1990 |
| EP | 0 706 040 A1 | 4/1996 |
| WO | WO 96/11399 | 4/1996 |
| WO | WO 97/38305 | 10/1997 |

* cited by examiner

Primary Examiner—Albert Gagliardi
(74) Attorney, Agent, or Firm—Hoffman, Wasson & Gitler

(57) ABSTRACT

The invention relates to a system for the on-line measurement of a parameter in a processing stream. The system comprises a scanning head mounted adjacent a continuous stream of processed material, the scanning head comprising a remote light source and reflected light gathering and transmission apparatus; a near infrared spectrophotometer which includes a monochromator for resolving the reflected light into light of a discrete wavelength; a database containing a reference calibration equation linking absorption characteristics by wavelength and the quantified presence of the parameter of interest; and a computer for measuring the parameter by application of the calibration equation to the obtained spectrum for a sample and managing said system. The invention also comprises a method of on-line measurement of a parameter in a processing stream by NIR spectroscopy and networks comprising systems according to the invention. The system and method of the invention are particularly suited to measuring a parameter of interest in processed sugar cane.

16 Claims, 4 Drawing Sheets

ON-LINE MEASURING SYSTEM AND METHOD

This invention relates to a system and method for measuring a parameter of interest in a processing stream. In particular, the invention relates to the use of near infrared spectroscopy for the on-line measurement of a parameter of interest in a processing stream. More particularly, the invention relates to the use of near infrared spectroscopy for the on-line measurement of parameters of interest in sugar cane processing.

BACKGROUND ART

Processing of biological material such as plant material usually involves measuring parameters of interest in the starting material and through to the desired end product or products. The measurement of the parameters can be for process control or for monitoring the level of a component in the material.

Measurements are typically made on samples taken from the processing stream. Depending on the parameter being measured, there can be a delay in determining the value of a parameter, as a consequence of which the parameter is not determined in real time. Furthermore, a sample may not be truly representative of the bulk of the material being processed at the point of sampling.

There can be other difficulties with measuring parameters of interest in a processing stream by sampling. A particular field where such difficulties occur is sugar cane processing. Sugar and related products are provided by processing sugar cane in sugar mills where the cane is crushed and processed through to crystalline raw sugar and molasses. The cane is supplied by plantation owners or individual cane farmers with the owners or farmers being paid for the cane supplied on the basis of tonnage and quality.

In Australia, for example, the amount paid to a plantation owner or farmer for each parcel, of the supplied cane is determined by weighing the parcel and evaluating the sugar content of the cane. An industry-agreed value is then used to calculate the amount paid for the parcel, the whole process being referred to as the "cane payment scheme". Various systems are used to determine the sugar content of the supplied cane. Each of the systems requires sampling, sample processing and analysis. In many countries, a core of cane is withdrawn from the delivered cane, processed by pressing or wet disintegration to juice which is analysed and converted to a measure of the sugar content of the cane.

The system used in Australia requires analysis of the earliest juice (first expressed juice) driven out of the cane crushing rollers. This entity has been shown to be convertible to and representative of the analysis of the whole cane. The cane payment system requires continuous sampling of the first expressed juice throughout the period of crushing each parcel of cane and an analysis reported for that parcel. Payment is based on this analysis and the weight of the parcel. The juice is subsampled and analysed according to standard proscribed methodologies for "pol" (a measure of the sucrose content of the juice) and "brix" (a measure of the dissolved solids content of the juice). The estimation of the total cane supply is determined by means of the first expressed juice analysis, the fiber content of the cane and empirically determined relationships linking the juice analysis and total cane analysis.

The fiber analysis of the cane for which the juice is sampled is determinable by washing a representative sample of the cane free of dissolved solids. The sample is prepared by cutter grinding to an appropriate fineness prior to washing. Sampling and analysis for individual parcels is not practical and a deemed fiber is used in calculations on an individual farmer's cane delivery.

Each variety of cane is allocated to one of two or three classes of more or less common average fiber composition. The deemed or "class fiber" as it is termed is a rolling average of the fiber of the class which has been allocated to the cane variety. The rolling average is obtained by regular sampling of each class throughout the day, compositing within the class and determination of the daily average fiber. Several days analyses are combined in the rolling average.

The use of class fiber is a particular weakness of the current system but is forced upon the system by financial and practical impossibility in providing a representative, meaningful individual fiber composition for each parcel of cane. Providing such representative and meaningful data in a typical Australian sugar mill would require the analysis of at least 150 parcels of cane each day, in duplicate, requiring a sampling team of approximately 30 persons, approximately 20 fiber analysing instruments and 4 to 5 cutter grinding machines.

The class fiber system also makes no distinction between the actual condition of the particular parcel of harvested cane in respect of dirt and extraneous matter content or in respect of inherent differences that may pertain to its plant or ratoon status.

Cane analysis is labour intensive and relies on extended sampling procedures, analysis and subsequent conversion to an estimate of the analysis of the whole cane received. The methodology in practical use does not give adequate feedback to the grower on cane quality or adequate feed forward for process control to the miller as it does not use individual parcel fiber analyses in the compositions.

Spectroscopy is a technique whereby a chemical compound can be identified by the degree of modification to light at different frequencies or wavelengths. Near infrared spectroscopy (NIR)—that is, spectroscopy where absorption of light over the range 400 to 2500 nm is analysed—has been previously applied as a tool in such fields as the measurement of protein and moisture in grain, the composition of forage for animal food, the degree of ripeness of fruit and the composition of fine cane particles, cane juices, syrups and sugars in sugar laboratory situations. However, NIR has not previously been exploited on-line for measuring parameters of interest in a processing stream such as comminuted sugar cane during cane processing.

SUMMARY OF THE INVENTION

The object of the invention is to provide a system and method for the on-line measurement of parameters of interest in a processing stream, which system and method utilise near infrared spectroscopy. A particular object of the invention is to provide a system and method for the on-line measurement of parameters of interest in sugar cane during processing of the cane utilising near infrared spectroscopy.

According to a first embodiment of the invention, there is provided a system for the on-line measurement of a parameter in a processing stream, the system comprising:

(a) a scanning head mounted adjacent a continuous stream of processed material, the scanning head comprising a remote light source and reflected light gathering and transmission apparatus;

(b) a near infrared spectrophotometer which includes a monochromator for resolving the reflected light into light of a discrete wavelength;

(c) a database containing a reference calibration equation linking absorption characteristics by wavelength and the quantified presence of the parameter of interest; and (d) a computer for measuring the parameter by application of the calibration equation to the obtained spectrum for a sample and managing said system.

According to a second aspect of the invention, there is provided a method of on-line measurement of a parameter in a processing stream, the method comprising the steps of:

(i) obtaining an infrared reflectance spectrum from a stream of processed material;

(ii) applying an appropriate calibration equation to the spectrum to quantify the presence of the parameter of interest; and (iii) statistically validating the spectrum obtained as being represented by the calibration equation.

According to a third embodiment of the invention, there is provided a system for the on-line measurement of a parameter in processed sugar cane, the system comprising:

(a) a scanning head mounted adjacent a continuous stream of processed cane, the scanning head comprising a remote light source and reflected light gathering and transmission apparatus;

(b) a near infrared spectrophotometer which includes a monochromator for resolving the reflected light into light of a discrete wavelength;

(c) a database containing a reference calibration equation linking absorption characteristics by wavelength and the quantified presence of the parameter of interest; and (d) a computer for measuring the parameter by application of the calibration equation to the obtained spectrum for a sample and managing said system.

According to a fourth aspect of the invention, there is provided a method of on-line measurement of a parameter in processed sugar cane, the method comprising the steps of:

(i) obtaining an infrared reflectance spectrum from a stream of said processed cane;

(ii) applying an appropriate calibration equation to the spectrum to quantify the presence of the parameter of interest; and (iii) statistically validating the spectrum obtained as being represented by the calibration equation.

The term "on-line" as used in the above definitions of embodiments and hereafter denotes measurement at the actual process stream as well as measurement on a portion of the stream of material being processed through a by-pass line. The second of the meanings given in the preceding sentence is commonly referred to as an "at-line" measurement.

The term "processing stream" as used in the definitions of the first and second embodiments of the invention denotes a stream of material derived from plants wherein the plant, or a part thereof, has been comminuted. Alternatively, plant-derived material can be material that has been extracted from a plant, or part thereof, by procedures such as slicing, dicing, shredding, mincing, pulping, pressing, sawing or rasping. The processing stream referred to in these embodiments thus includes, but is not limited to, prepared or comminuted sugar cane, sliced sugar beet, crystal sugar, bagasse at various stages, silage and processed grains, fruit and vegetables as well as processed fruit and vegetables, particle board and paper.

It will be appreciated from the foregoing description of the third and fourth embodiments that the invention allows on-line assessment of cane quality providing, in contrast to present measurement systems, meaningful fully representative information. Parameters of interest which can be measured using the system and method of the invention include fiber content, juice brix or dissolved solids content, juice polarisation or sugar content, commercial sugar content or CCS of cane, water, and other quality parameters such as ash which is related to dirt content, individual inorganic elements, and process parameters such as pol in open cells. The inorganic parameters that can be measured include the following: phosphate; nitrogen; calcium; magnesium; potassium; iron; and, silicon. Extraneous matter such as dirt, tops, trash and suckers can also be measured.

The term "processed sugar cane" or derivatives thereof as used herein include within their scope, prepared cane, intermediate and final crushing roller bagasse, boiler feed materials, raw sugar and crystalline sugar. Consequently, in addition to the parameters given above, other parameters that can be measured include pol, moisture, grist, filterability, starch, dextran and other polysaccharides.

The continuous stream of processed cane can be a stream included in a normal sugar milling process or can be a stream set up for analytical purposes. In other words, the invention is not restricted in application to the milling process per se. An example of a stream set up for analytical purposes is processed cane from core samples of cane batches, which samples are processed in a mill's analytical laboratory.

A requirement of the stream, however, is that the material be devoid of gross voids so that the scanning head sees an essentially unbroken layer of the processed cane. If necessary, the conduit or the like carrying the stream can be constricted to effect a compression of the material passing the scanning head.

In the system and method of the invention, the scanning head is mounted at a fixed distance from the surface of the processing stream, which, in the case of the third and fourth embodiments, is a stream of processed cane. The distance between the surface of the processing stream and the scanning head is usually fixed within the range of 75 to 100 mm with the distance maintained at ±5 mm. Maintenance of a set distance is necessary for accurate application of calibration equations to parameter measurement.

As an example of the mounting of the scanning head in sugar cane processing, the head is mounted at the feed chute for the first crushing mill of a raw sugar mill. Other suitable positions for mounting the scanning head on equipment included in a sugar mill will be detailed below.

A suitable cradle may be required for mounting the scanning head to insulate the head from vibration present in the equipment comprising the process. This is particularly the case with sugar milling equipment. Temperature control is also advantageous such as by mounting the scanning head in an air-conditioned chamber. As a window has to be provided for light transfer between the scanning head and the processed cane, the sensing head cradle preferably allows repositioning of the sensing head so that the window glass can be removed for cleaning or replacement. Cleaning or replacement of the window glass is necessary as debris from a processing stream such as processed cane passing the window can build up on the glass or damage the glass, interfering with operation of the system.

The spectrophotometer is preferably remote from the scanning head but linked thereto by a fiber optic cable. The spectrophotometer, like the sensing head, is vibration and temperature insulated if necessary. When remotely located, the requirements of the vibration insulation means in respect of the spectrophotometer are not as stringent as for the sensing head. However, the sensing head and spectrophotometer can be an integral unit in which case the vibration and temperature insulation must meet the requirements of the sensing head. Any insulated chamber housing the spectrophotometer is advantageously airconditioned.

The spectrophotometer can be any suitable commercially available instrument. An example of a suitable instrument is Foss NIRSystems Model 6500 system incorporating a Model 6500 monochromator, Direct Light Reflectance System and ISI NIRS3 or Vision Software supplied by Foss NIRSystems Inc, 121021 Tech Rd, Silver Spring, Md. 20904, USA. This instrument has a scanning range of 400 to 2,500 nm. However, another suitable instrument is the NIRSystems Model 5000 which operates over a wavelength range of 1,100 to 2,500 nm.

The database calibration equations referred to in section (c) of the above definitions of the first and third embodiments can be determined by the gathering of reflectance spectra on the material present in the processing stream and statistically evaluating the data using a routine laboratory assay of the parameters of interest on concomitant samples of the material. A minimum of 200 assay samples are generally required for equation development and inclusion in the database. The interfaced computer referred to in section (d) of the first and third embodiments serves to link the analytical system with the individual user of the data or the dependent processes. In the case of prepared cane, it is necessary that the instrument be linked to the cane sample tracking system to provide cane parcel identification for the cane being scanned and to have the capability of inserting the result of the computations for parameters of interest into the files in the cane payment system for the relevant parcel of cane. The computer software advantageously has the capability of delivering analytical data to process controllers in real time.

The calibration equations are crucial to the operation of the system and the method but can nevertheless be developed by one of ordinary skill in the art, particularly with the guidance of the NIR instrument manufacturer. The process involves the steps of collection of spectral and laboratory data, population structuring, calibration development and finally, validation of the equation. It is essential that the link between the spectral data and the corresponding laboratory analysis is strong. Using sugar cane processing as an example, the spectral data is collected by scanning the portion of cane as it passes the read head, collecting all spectra associated with that portion and averaging them to produce a single spectral result for that portion. The corresponding laboratory sample, in the case of calibration for fiber, is obtained by taking small snap samples from the process stream over the whole length of the portion. These snaps are thoroughly mixed to produce an average laboratory sample, which is then sub-sampled for analysis by a laboratory can fiber machine or a laboratory bag fiber analysis procedure. A minimum of 200 such pairing of analyses of portions of cane are required to produce a preliminary equation. To produce a robust global equation, cane should be sampled which contains as much as possible of the likely variation in cane. The calibration software is used to determine the population boundaries of the calibration set which is necessary to define the spectra which are represented by the calibration equation to be developed. Spectra three standard deviations from the mean spectral result are discarded. The software selects the calibration set and the validation set from the spectra and their laboratory results. The calibration equation is developed from the calibration set using, for example, partial least squares calibration mathematics. The equations are validated, firstly, by applying the equation to the validation set and then in an on-line situation with spectra that were in no way associated with the calibration process.

A "local" calibration technique can also be employed. This calibration technique uses the library developed in the population structuring step in an on-line situation to select similar spectral results to an unknown spectrum obtained from a scan. These spectra and results are used to develop an equation which is then applied to the unknown spectrum. This approach is particularly effective in a system of networked spectrophotometers employing the advantages in robustness of the global calibration with the precision of a local calibration.

As indicated above in the definition of the second and fourth embodiments, a preliminary step in the method of the invention is the obtainment of an infrared reflectance spectrum of the processing stream containing the parameter of interest. An objective in this step is to minimise the time taken to complete a scan so that more scans which are, in effect, sub-samples can be taken during the measurement of a particular parameter during the processing of a portion of material of interest.

Using measurement of a parameter in processed sugar cane as an example, scanning of a sample is initiated on receipt of instructions from a computer controlling the scanning operation, which computer is also central to the execution of the method. The term "sample" in the foregoing context denotes the measurement of a parameter in a particular portion of the processed material and in determining parameters in crushed cane, this portion will be what is referred to as a "parcel" or a "rake" of cane. In a typical scan of about 36 seconds duration, about 26 seconds is taken up in acquiring up to 32 full spectral passes and 9 to 10 seconds for signal transfer. Scan frequency can be increased to allow more time for scanning the process material. The signal to noise ratio is optimised by assessing individual scans and corrupted scans discounted. Corruption, for example, can be due to voids in the crushed cane passing the scanning head.

Depending on the time taken for a parcel to pass the scanning head, any scans obtained can be computed with the calibration equations and the results averaged to give a representative parameter value for the parcel.

The computer referred to in sub-paragraph (d) of the definition of the first and second embodiments can also serve to manage signals received thereby and in presentation of appropriate information from the database. It will be appreciated that normally there would be interest in more than one parameter in the processing stream. Consequently, the database must hold a reference calibration equation for each of those parameters. For example, in sugar cane processing, % fiber, brix and % water are measured in the initial crushed cane. Spectral integrity is checked and the validity of predicted results can be assessed by determining that the sum of these values is 100±5. The computer, through its control program, liaises with the mill's cane payment and process control computers taking current information and monitoring scanning conditions. It initiates a scan through the scan program when conditions are conducive. The scan program starts the instrument scan and receives the spectrum when the scan is completed. The scan program is used to apply the calibration equation for the component of interest to calculate a result from the spectrum which is passed to the control software with its evaluation of the conformity of the spectrum obtained to the spectra in the calibration set. The control software inspects and validates the results. If the result is accepted, it updates process control signals and cane payment details, computing averages for the rake when the rake ends and passing average results from accepted scans to the cane payment computer.

In the method of the second and fourth embodiments of the invention, step (iii) can additionally comprise calling for physical sampling should a measured spectrum lie outside the range predicted by a calibration equation. That is, if an unusual spectrum is obtained, a sample can be obtained for measurement of the parameter of interest by routine analytical procedures.

The system according to the first and third embodiments of the invention can be incorporated into a network. In such a network, a centralised database provides reference calibration equations to other processing streams in the network. Further, provided that instruments are standardised against the instrument on which the calibration equations were developed, the latter instrument can be used as a master instrument within the network. Global reference calibration equations provide a calibration which is robust to changes in processing stream characteristics, avoiding taking additional calibration samples and is a feature of the network arrangement.

A network of systems according to the invention is particularly advantageous in measuring parameter of interest in sugar cane processing. In this industry, sugar mills in particular region may be part of a network. Application to the network of a system according to the third embodiment facilitates operation of the mills, with fully interchangeable instruments, in such a manner as to use common calibration equations or allow access to a suitable equation from the network to apply to cane with unfamiliar characteristics and is particularly advantageous for the cane payment system discussed above.

Having broadly described the invention, the system and method will now be exemplified with reference to the accompanying drawings.

BEST MODE FOR CARRYING OUT THE INVENTION

Figure 1:
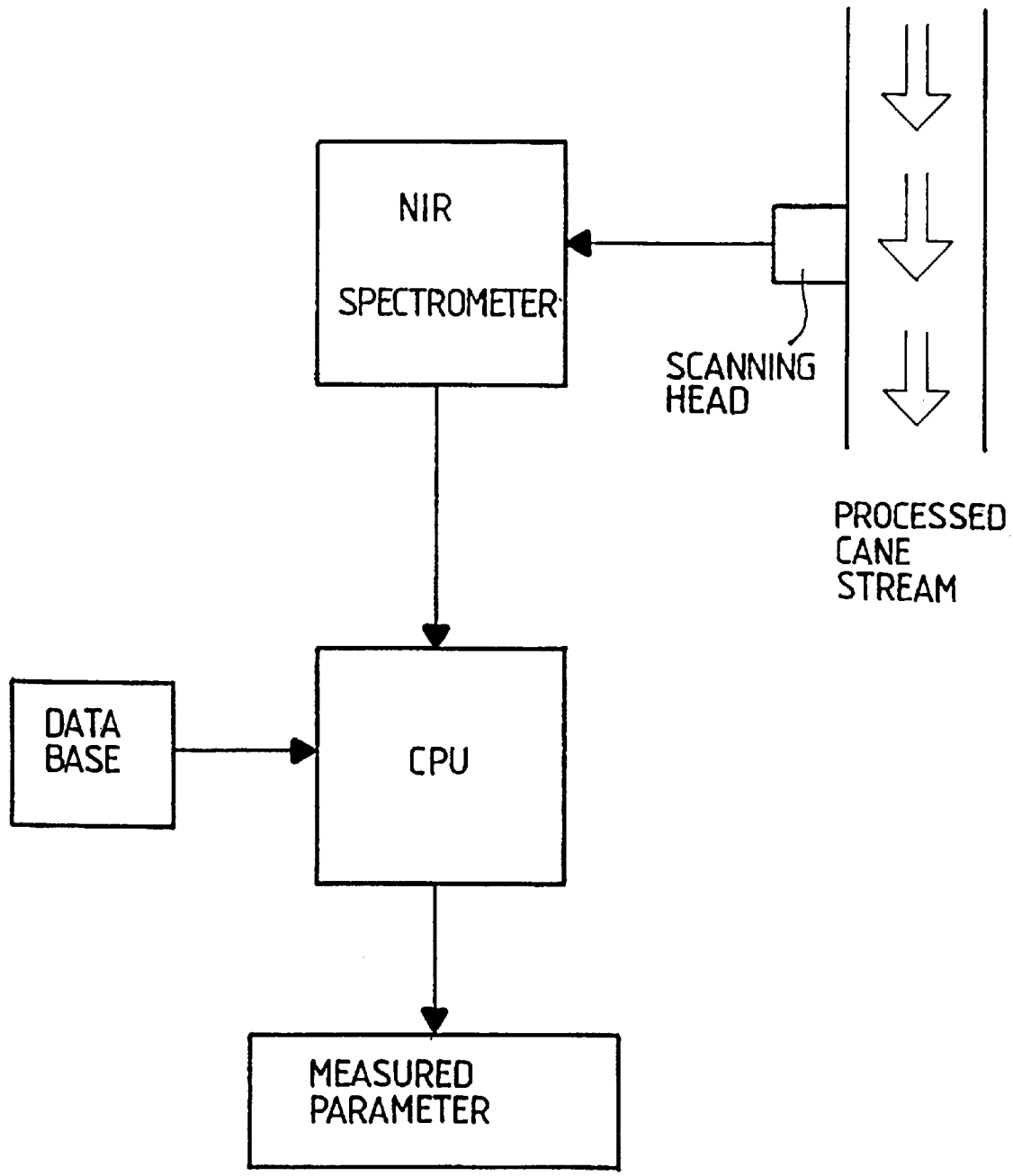
FIG. 1 is a schematic representation of a system according to the invention applied to the measurement of parameters in sugar cane processing.

FIG. 1 is a schematic drawing of the system. The scanning head of the direct light reflectance system of a NIR Monochromator class of spectrophotometer is positioned alongside of or above a process stream to be analysed. Reflected light passes by way of fiber optics to the spectrophotometer where the light is broken into wavelengths over the range 400 to 2500 nm in steps of typically 2 nm. A spectrum of the absorption by the process stream, by wavelength, is produced for each scan of the sample. A database of calibration equations is stored for each parameter of interest such as fiber content in the process stream. This information is held available for access by the CPU. The database also stores the characteristics of the spectra used in deriving the calibration equations. An average spectrum is produced for each sample scan. The relevant sections of the spectrum for the calibration of interest are extracted and computed to deliver the measured parameter for the scan. The results from all the accepted scans of the relevant portion of the process stream are averaged for the prediction. The spectrum obtained is useable for as many parameters as calibrations are available. The CPU can reject a spectrum that does not conform to the set of spectra used to derive the calibration equation.

Figure 2:
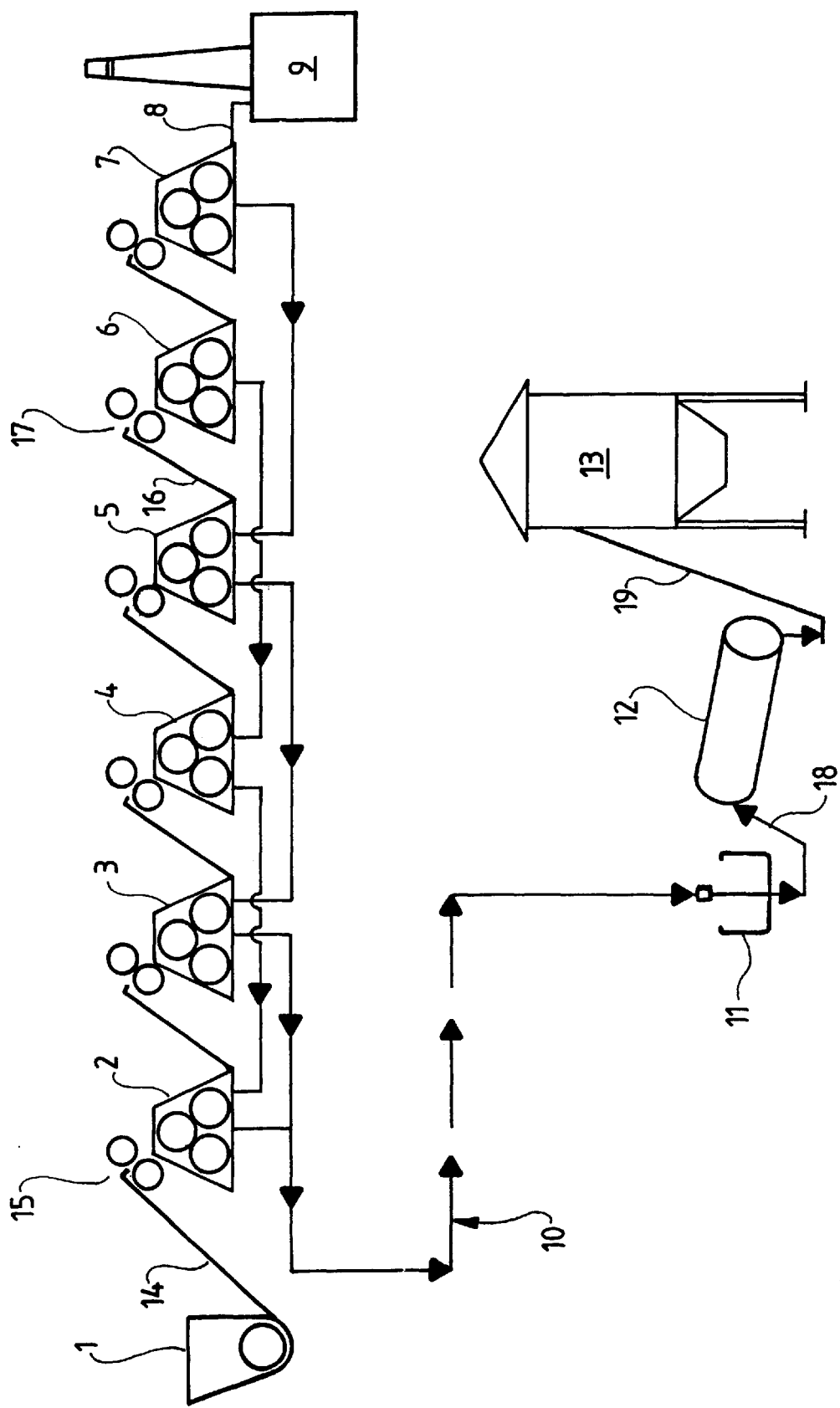
FIG. 2 is a schematic diagram of a sugar mill showing where parameters of processed sugar cane can be measured during processing of sugar cane and sugar.

Turning to FIG. 2, there is schematically shown portions of a sugar milling process. In the figure, a hammer mill shredder 1 is shown followed by a series of crushing rollers, 2 to 7. Bagasse—residue cane fiber—is taken away from the final crushing roller 7 by conveyor 8 to be used, for example, as fuel in the mill power house 9. Cane juice from the milling train 10 is further processed through to final steps which include centrifugation 11 and drying 12 from which raw sugar is transported to a storage bin 13.

Parameters of interest can be measured using the system of the invention with the scanning head installed in the following process streams: at the beginning 14 or end 15 of the feed chute from hammer mill 1 to the first set of crushing rollers 2; at the beginning 16 or end 17 of feed chutes between successive sets of crushing rollers such as indicated between crushing rollers 5 and 6; the conveyor 8 which transports bagasse away from milling train 10; the line 18 carrying crystalline sugar from centrifugal 11 to drier 12; and, the conveyor 19 carrying dried sugar to storage bin 13.

Figure 3:
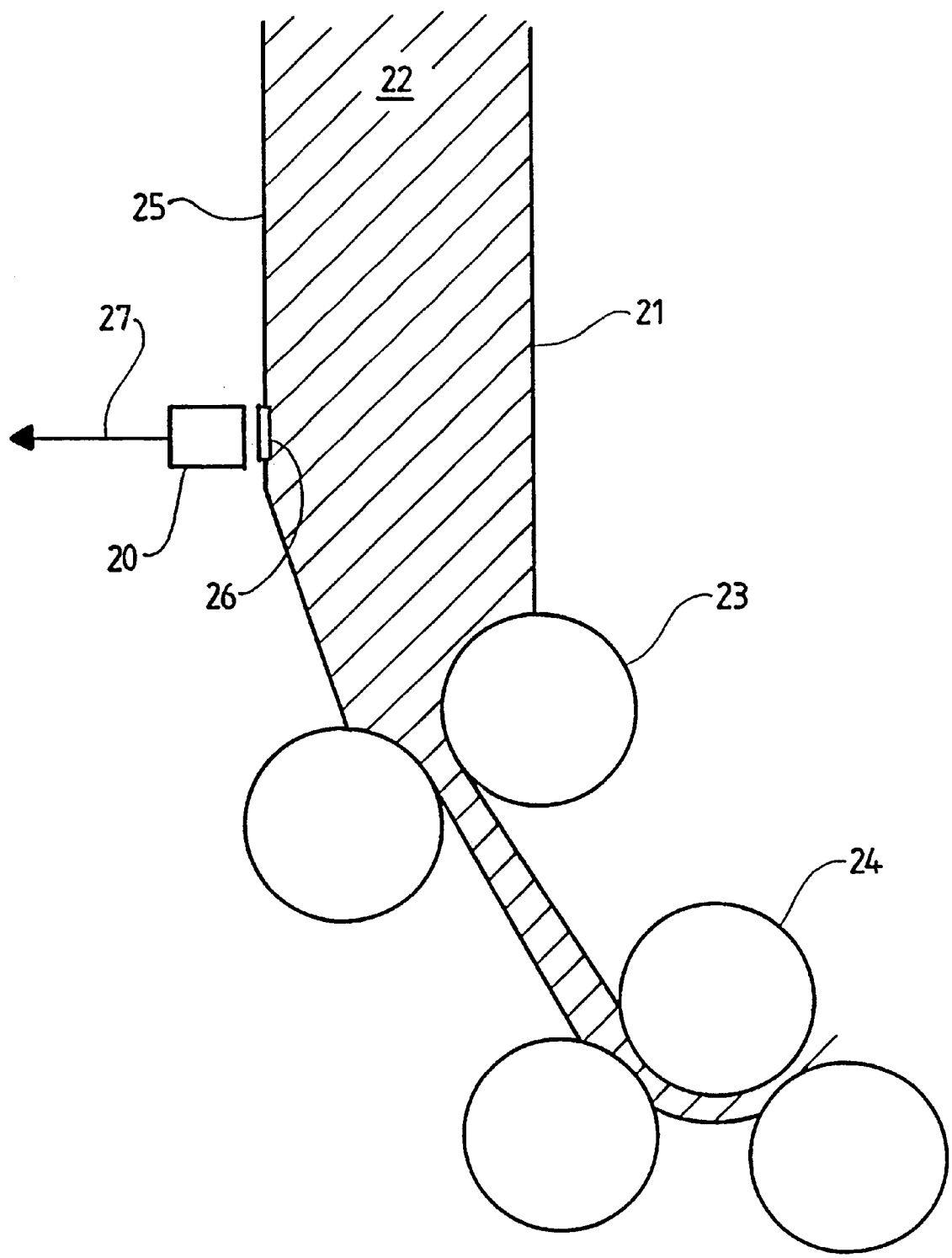
FIG. 3 is a schematic showing the positioning of a scanning head with respect to a chute supplying cane to crushing rollers.

FIG. 3 is a schematic representation of the mounting of a scanning head 20 to a feed chute 21 supplying crushed cane 22 to first pressure feeder rollers 23 and mill rollers 24 which collectively form one of the sets of crushing rollers referred to above in connection with FIG. 2. Scanning head 20 is mounted to a wall 25 of feed chute 21 with a viewing window 26 between the head and the interior of the chute. Viewing window 26 is demountable for replacement or cleaning. A fiber optic cable 27 transmits light from head 20 to a spectrophotometer not shown in the drawing. The mounting of head 20 to chute wall 25 is such that the distance between the head and the interior of the chute is fixed.

Figure 4:
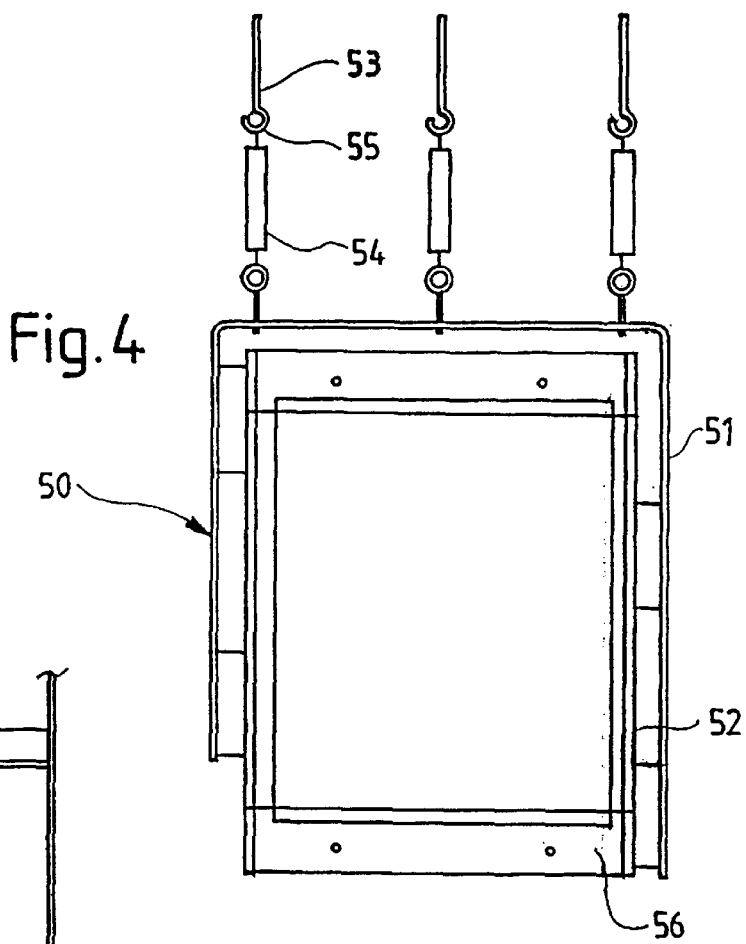
FIG. 4 is a perspective view of a cradle for the NIR spectrophotometer.

FIG. 4 shows a cradle for the NIR spectrophotometer of the system shown in FIG. 1, which cradle minimises transmission of vibration from mill equipment to the NIR instrument. The cradle 50 includes a hanging bracket 51 and an instrument mounting bracket 52. Hanging bracket 51 is suspended from any suitable overhead structure by a plurality of cables and springs, one such combination being indicated at 53 and 54, respectively. Each cable terminates with a hook, one of which is indicated at 55, for ease of demounting the cradle. High frequency dampers are provided, one being indicated at 56, for connecting instrument bracket 52 to hanging bracket 51. Four dampers are typically used. A suitable type of damper is a model WR5-400-10-S-M obtainable from Hawker Richardson Limited of Garden Square, Macgregor Road, Mt Gravaft, Queensland, Australia.

Figure 5:
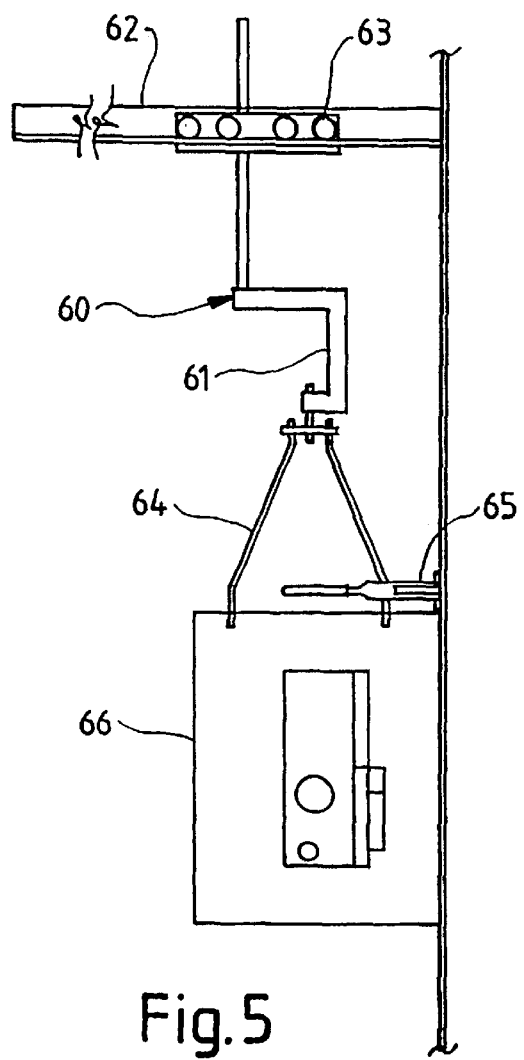
FIG. 5 is a perspective view of a cradle for the scanning head.

A scanning head cradle is shown in FIG. 5. The cradle permits efficient displacement of the scanning head (in its housing—see below) for cleaning or maintenance of the window glass while allowing precise return of the scanning head to its scanning position.

FIG. 5 shows cradle 60 comprising hanging bracket 61, a channel 62 for a trolley assembly 63, a plurality of hanger rods one of which is indicated at 64, toggle clamps 65, and a housing 66 for the scanning head. Channel 62 extends from the wall of the conduit for processed cane with which the scanning head is associated. The trolley assembly 63 allows the cradle to be moved away from the wall once clamp 65 has been released. The hanger rods are pivotally connected to hanging bracket 61 so that housing 66 can be pivoted once the cradle has been moved away from the conduit wall. In an alternative arrangement, the components of FIG. 5 can be provided with a sealed controlled environment enclosure (not shown) mounted on the chute.

Figure 6:
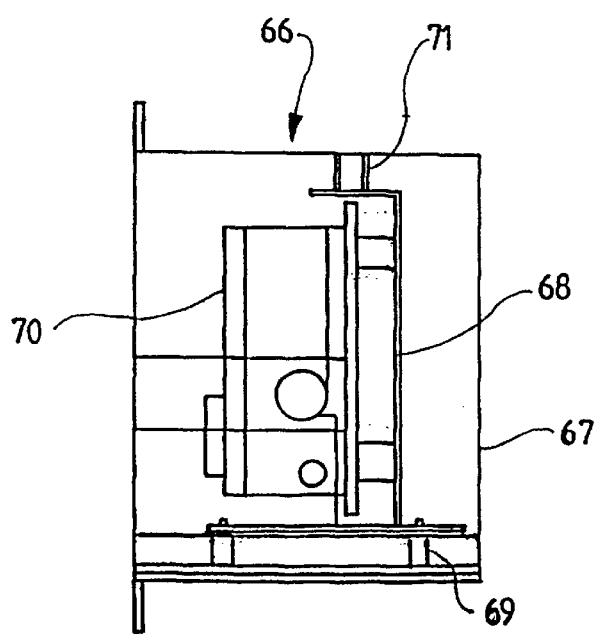
FIG. 6 is a cross sectional view of a housing for the scanning head.

Housing 66 is shown in more detail in FIG. 6. The housing is essentially a box having an open face 67 which abuts the wall of the conduit in the area which includes the window. Housing 66 includes six low frequency dampers (model WR2-800 from Hawker Richardson) which support a mounting bracket 68. One such low frequency damper is indicated at 69. The scanning head assembly 70 is mounted to bracket 68 via two high frequency dampers (WR4-400-10-S-M, again from Hawker Richardson), one of which is indicated at 71. Selection of dampers is made according to the weight of the piece to be protected and the vibration experienced. A spring can be provided between the top of housing 66 and a base plate at the bottom end of mounting bracket 68. This spring shifts the loading between the top and bottom low frequency dampers. Alternatively, various thickness insertion rubbers can be placed under the bottom end of the mounting bracket for the same purpose.

The hanging bracket of the cradle described in FIG. 5 is not essential, it will be appreciated, and housing 66 can be mounted directly to a wall of the conduit for processed cane provided that appropriate vibration dampening is used in the mounting. The mounting must of course be such that demounting of the housing is possible to allow access to the window in the conduit wall.

Examples of the application of the system and method to the measurement of cane quality parameters follow.

EXAMPLE 1

Measurement of Cane Quality Parameters

In this example, we describe the development of calibration equations for parameters of interest in prepared cane and in raw sugar. The example also verifies the accuracy of the method and verifies that the method is suitable for on-line factory use.

In this work, a process stream was sampled concurrently with scanning of the stream using the near infrared 6500 system referred to above. The sugar mill's normal cane tracking system was used to follow the cane through the process, identifying the cane at the scanning window and ensuring sample correspondence at the prepared cane and first expressed cane juice sampling positions.

First expressed juice was sampled continuously over the period of crushing of the cane parcel under study. This juice was analysed by routine laboratory methods for the entities of the sugar industry, brix, and polarisation, and for additional substances such as nitrogen, phosphorus, alcohols and so forth.

The prepared cane was sampled over a concomitant period to the juice sample by means of the taking as many "snap" samples as possible during the passage of a parcel of cane from a purpose built hatch in the ducting for the process stream. As indicated, the time relativity of the sampling positions was maintained by the cane tracking system, but, typically, the fiber hatch was adjacent the near infrared scanning position to simplify management of the process. A grab sample may be taken and unused material cleared away in 30 second cycles. Consequently, a parcel requiring 20 minutes for crushing was sampled by 40 snaps into a suitably sized bin. The bin was sealed until further processing, which processing was generally completed within one hour.

The prepared cane sample was mixed and cutter ground to a sample suitable for analysis. Mixing was accomplished by hand. In this operation, the bulk sample was split into two heaps and handfuls from each heap were intimately mixed, during which process lumps were broken up, into a common mass. The heap so obtained was rotated 900, split and remixed and then rotated, split and further mixed. The resultant mass was then spread thinly to a thickness of about 2 cm and approximately 3 kg of the mixture was randomly taken for cutter grinding. In this step, care was taken to sub-sample through to the bottom of the layer. Cutting grinding was achieved using one the standard devices of the Australian industry, the JEFFCO Cutter Grinder supplied by Jeffress Engineering of Northgate, Brisbane, Queensland.

The cutter ground material was again thoroughly mixed by the sequence described for prepared cane. Sub-samples were taken for duplicate fiber content and duplicate moisture determination in accordance with standard industry methods. Both bag and can fibers were obtained.

The process stream was scanned through a scanning window by means of a near infrared spectrophotometer in remote reflectance mode. Some of the absorption spectra were taken in cycles of 1 minute 18 seconds. In this time, the instrument completed and averaged 32 full spectral passes of the sample (which was travelling past the sensor at approximately 0.5 m/sec) and completed and averaged 32 full spectral passes of a ceramic reference tile, then processed and transmitted the data. The remaining data was obtained at the rate of 36 seconds for 32 full passes.

The transmitted spectrum for a scan was obtained by subtracting the averaged reference scan from the averaged sample scan. The reference scan helped account for environmentally induced noise and confirmed the instrument was maintaining normal operation.

The spectrum related absorption (defined as $\log_{10}$ (1/reflectance) ) to user selected wavelength bands drawn from the entire range 400 to 2500 nm. The absorption was resolved into 2 nm increments.

In calibration mode, the spectral scans which were taken during the passage of the calibration sample were averaged and stored together with the routine laboratory analyses for the parameters of interest. The assembled calibration samples provided a suite of paired spectral lines and analyses. ISI, NSAS or Vision software, provided by the instrument manufacturers, Foss NIRSystems, was used to process the data to calibration. ISI has predominated in this work. ISI uses the first derivative with respect to wavelength of the average spectral line and equivalent average of routine analysis for the sample to build up a calibration equation over all the calibration samples. ISI uses a modified partial least squares (PLS) analysis resulting in a linear equation with coefficients on wavelength in 2 nm steps. The technique builds an equation for the component in question and the spectra may be reused for derivation of a calibration equation for another component of the same sample set. The technique is also referred to as principal component analysis. For cane payment purposes, many thousands of assays have been conducted to enhance the reliability of the result prediction equations.

The calibration equation in two nm wavelength steps was used to predict a component's presence from the spectrum of an unknown passing the sampling point.

The software has the capability of determining when the spectral result lies within a population known to give accurate predictions. This capability was used at the calibration stage to identify "deformed" spectra prompting a check as to whether the deformity was due to excessive voids in the sample at the time, whereupon the spectrum was removed from consideration, or that it was outside the known population and needed to be analysed conventionally for inclusion.

In an on-line situation, the software can call for a sample to be taken if a spectrum lies outside expectations. The incorporation or not of this sample in the calibration will be post processed on the basis of inspection of the process and the spectrum.

A calibration equation was derived and thereafter sampling was continued to fill in gaps in the spectral coverage and expand the range of routine laboratory values in the calibration equation. The following tables provide statistical data for the routine laboratory and NIR analyses of cane quality parameters. The data show that the technique of NIR spectroscopy may be successfully used, on-line, in the generation of calibration equations that are robust and result in representative analyses of the cane quality parameters.

Table 1 provides a reference with which to compare the NIR results. It presents the error statistics for the routine laboratory analyses of cane quality parameters. The tables which follow present the statistical characteristics of the calibration equations developed, their application generally, and in a particular mill. In these tables, standard errors were calculated using the standard deviation of the difference between results.

Table 2 refers to the "global equation" developed in the experimentation in a number of mills over a number of crushing seasons using three NIRSystems 6500 instruments. The global equation is a generic equation to be applied in any milling situation requiring minimal calibration development. A mill-particular calibration would require significant calibration development on first use and most likely with each change of cane characteristic due to seasonal or growing conditions. In Table 2, the performance of the equation is shown pooled over all the mills used in calibration development. Both the calibration statistics and the statistics arising from on-line use (validation) are given in the table.

Tables 3 to 7 show the use of the global equation in each of the mills for which calibration data was provided. The robustness of the equations are highlighted by the consistency in prediction performance from one mill to the next.

Table 8 presents the statistics for useful calibration equations derived at one mill but not yet extended to other mills or in numbers sufficient for the calibration equation to be classified as global.

Overall, the results show a strong agreement between a NIR prediction and the result obtained by routine laboratory means.

The sugar industry's analytical measure, Commercial Cane Sugar (CCS) is derived in current practice by an empirical formula linking the cane fiber content and the analysis of the first juice expressed from the cane. The invention may be used to predict the CCS directly, if desired, and this is the analytical result designated "Individual CCS". The error associated with the normal computation of CCS is not known. However, extrapolation from errors in the fiber and juice analyses techniques would lead to a best expected laboratory standard error of approximately 0.33. In practice however, the reported CCS is derived from an assumed fiber estimation which may be substantially incorrect and actual, in use, errors will be substantially higher than 0.33. It would be substantially higher than that which would be obtained from the Individual CCS calibration equation or from near infrared spectroscopy prediction of fiber and calculation of CCS in the normal manner.

The near infrared method as exemplified is thus, because of its on-line capability, substantially more reliable than is possible with current practice.

TABLE 1

Laboratory Duplicate Statistics for Prepared Cane samples Used In NIR Calibration

| Constituent | Standard Error | Correlation Co-efficient | Slope | Bias | Range (%) | Number of Samples |
|---|---|---|---|---|---|---|
| Can Fibre | 0.22 | 0.984 | 1.00 | 0.00 | 11.9–23.6 | 1226 |
| Combustion Ash | 0.06 | 0.998 | 1.00 | 0.00 | 0.50–10.50 | 1400 |
| Dry Matter | 0.24 | 0.987 | 1.00 | −0.01 | 23.3–38.4 | 1145 |
| Pol in open cells | 1.71 | 0.873 | 0.97 | 0.00 | 75.8–95.0 | 116 |
| Nitrogen in Juice (mg/L) | 29 | 0.85 | 0.95 | 0 | 188–615 | 33 |
| Phosphate in Juice (mg/L) | 15 | 0.975 | 0.976 | 2.3 | 23.8–354 | 565 |
| Potassium % cane | 0.006 | 0.973 | 1.02 | −0.002 | 0.07–0.22 | 27 |
| Calcium % cane | 0.003 | 0.869 | 1.01 | 0.003 | 0.01–0.04 | 27 |
| Silica % cane | 0.04 | 0.998 | 0.996 | −0.01 | 0.22–3.4 | 27 |
| Magnesium % cane | 0.002 | 0.914 | 0.978 | −0.001 | 0.01–0.03 | 27 |
| Insoluble Ash | 0.1 | 0.992 | 1.016 | 0 | 0.51–5.43 | 91 |

TABLE 2

Global NIR Equation Statistics for Prepared Cane in Calibration
and Validation for Pooled Data from 5 Mills and 3 Instruments Over 3 Seasons

| | Calibration Statistics | | | | Validation Statistics | | |
|---|---|---|---|---|---|---|---|
| Constituent | Standard Error | Correlation Co-efficient | Range (%) | Number of Samples | Standard Error | Correlation Co-efficient | Slope |
| Fibre | 0.518 | 0.865 | 11.77–20.33 | 556 | 0.71 | 0.763 | 0.92 |
| Pol in juice | 0.444 | 0.961 | 10.90–23.52 | 3089 | 0.48 | 0.969 | 1.03 |
| Brix in juice | 0.437 | 0.957 | 14.00–25.90 | 3103 | 0.45 | 0.941 | 1.01 |
| Individual CCS | 0.339 | 0.952 | 9.01–17.13 | 1169 | 0.33 | 0.957 | 1.01 |
| Combustion Ash | 0.443 | 0.782 | 0.36–6.97 | 1340 | 0.50 | 0.705 | 1.00 |
| Dry Matter | 0.57 | 0.916 | 26.84–38.55 | 1217 | 0.61 | 0.906 | 1.02 |
| Pol in open cells | 0.655 | 0.918 | 80.63–92.73 | 89 | 1.81 | 0.588 | 0.81 |
| Phosphate in Juice (mg/L) | 5.40 | 0.925 | 23.79–126.1 | 92 | 20.56 | 0.85 | 0.99 |

TABLE 3

Global NIR Equation Statistics for Prepared Cane In Prediction at Mill 1 over 3 Seasons Using Instruments 1 and 2

| | Validation Statistics | | | | | |
|---|---|---|---|---|---|---|
| Constituent | Standard Error | Correlation Co-efficient | Slope | Bias | Range (%) | Number of Samples |
| Fibre | 0.68 | 0.769 | 1.01 | 0.19 | 11.90–20.20 | 651 |
| Pol in juice | 0.48 | 0.958 | 1.04 | 0.12 | 9.20–25.90 | 14804 |
| Brix in juice | 0.47 | 0.917 | 1.00 | 0.01 | 12.10–24.90 | 14830 |
| Individual CCS | 0.39 | 0.931 | 1.04 | 0.10 | 7.74–15.85 | 928 |
| Combustlon Ash | 0.52 | 0.672 | 1.05 | 0.00 | 0.78–6.90 | 805 |
| Dry Matter | 0.65 | 0.879 | 1.00 | −0.09 | 25.9–36.15 | 1010 |
| Pol in open cells | 1.81 | 0.588 | 0.81 | −0.20 | 81.0–93.0 | 120 |

TABLE 4

Global NIR Equation Statistics for Prepared Cane in Prediction at Mill 2 Over a Six Week Period Using Instrument 1

| | Validation Statistics | | | | | |
|---|---|---|---|---|---|---|
| Constituent | Standard Error | Correlation Co-efficient | Slope | Bias | Range (%) | Number of Samples |
| Fibre | 0.54 | 0.922 | 1.01 | 0.24 | 12.62–16.92 | 29 |
| Pol in juice | 0.48 | 0.91 | 0.86 | 0.03 | 12.0–19.9 | 2154 |
| Brix in juice | 0.46 | 0.9 | 0.87 | −0.03 | 14.8–22.2 | 2154 |
| Individual CCS | 0.34 | 0.865 | 0.88 | 0.21 | 10.34–13.57 | 53 |
| Combustion Ash | 0.54 | 0.833 | 1.11 | −0.02 | 0.65–6.54 | 338 |
| Dry Matter | 0.60 | 0.868 | 1.00 | 0.04 | 27.07–34.96 | 178 |

TABLE 5

Global NIR Equation Statistics for Prepared Cane in Prediction at Mill 3 Over a Six Week Period Using Instrument 2

| | Validation Statistics | | | | | |
|---|---|---|---|---|---|---|
| Constituent | Standard Error | Correlation Co-efficient | Slope | Bias | Range (%) | Number of Samples |
| Fibre | 0.53 | 0.862 | 0.91 | 0.10 | 13.38–20.23 | 104 |
| Pol in juice | 0.38 | 0.96 | 1.00 | 0.13 | 10.9–22.2 | 2024 |
| Brix in juice | 0.39 | 0.95 | 0.97 | 0.04 | 14.2–24.4 | 2024 |
| Individual CCS | 0.31 | 0.956 | 1.02 | −0.01 | 9.10–16.07 | 203 |
| Combustion Ash | 0.35 | 0.654 | 0.81 | 0.03 | 0.84–3.36 | 65 |
| Dry Matter | 0.51 | 0.911 | 1.04 | −0.01 | 28.59–36.83 | 152 |

TABLE 6

Global NIR Equation Statistics for Prepared Cane in Prediction at Mill 4 Over a Six Week Period Using Instrument 2

| | Validation Statistics | | | | | |
|---|---|---|---|---|---|---|
| Constituent | Standard Error | Correlation Co-efficient | Slope | Bias | Range (%) | Number of Samples |
| Fibre | 0.71 | 0.62 | 1.06 | −0.20 | 9.3–17.7 | 116 |
| Pol in juice | 0.43 | 0.94 | 1.07 | −0.04 | 11.44–22.0 | 1881 |
| Brix in juice | 0.42 | 0.92 | 1.05 | −0.03 | 14.85–24.9 | 1881 |
| Individual CCS | 0.36 | 0.906 | 1.02 | 0.05 | 9.73–14.47 | 116 |
| Combustion Ash | 0.44 | 0.688 | 0.75 | −0.02 | 0.76–4.14 | 88 |
| Dry Matter | 0.66 | 0.81 | 1.01 | 0.00 | 27.52–33.45 | 108 |

TABLE 7

Global NIR Equation Statistics for Prepared Cane in Prediction at Mill 5 Over A Six Week Period Using Instrument 3

| | Validation Statistics | | | | | |
|---|---|---|---|---|---|---|
| Constituent | Standard Error | Correlation Co-efficient | Slope | Bias | Range (%) | Number of Samples |
| Fibre | 0.54 | 0.64 | 0.75 | −0.05 | 13.0–16.68 | 114 |
| Pol in juice | 0.49 | 0.89 | 1.13 | 0.07 | 15.2–24.0 | 1396 |
| Brix in juice | 0.46 | 0.89 | 1.14 | 0.11 | 18.2–25.9 | 1396 |
| Individual CCS | 0.38 | 0.9 | 1.21 | 0.02 | 12.44–17.13 | 74 |
| Combustion Ash | 0.30 | 0.4 | 0.50 | −0.02 | 0.7–2.22 | 115 |
| Dry Matter | 0.49 | 0.873 | 0.99 | 0.02 | 30.84–36.60 | 67 |

TABLE 8

Calibration Statistics for Prepared Cane Constituents Not Yet Considered Global

| | Calibration Statistics | | | |
|---|---|---|---|---|
| Constituent | Standard Error | Correlation Co-efficient | Range (%) | Number of Samples |
| Nitrogen in Juice (mg/L) | 24.127 | 0.938 | 188.0–630.0 | 33 |
| Potassium % cane | 0.003 | 0.99 | 0.07–0.22 | 27 |
| Calcium % cane | 0.001 | 0.997 | 0.01–0.04 | 27 |
| Silica % cane | 0.036 | 0.998 | 0.21–3.40 | 27 |
| Magnesium % cane | 0.001 | 0.995 | 0.01–0.03 | 27 |
| Insoluble Ash | 0.207 | 0.905 | 0.51–3.04 | 43 |
| Soluble Ash | 0.066 | 0.501 | 0.27–0.60 | 43 |

It will be appreciated that while the system and method according to the invention has been,exemplified in relation to the processing of sugar cane, they are broadly applicable to any other plant derived material in accordance with the first and second embodiments.

What is claimed is:

1. A system for the on-line measurement of a parameter in processed sugar cane, the system comprising:
   (a) a scanning head mounted adjacent a continuous stream of processed cane, the scanning head comprising a remote light source and reflected light gathering and transmission apparatus;
   (b) a near infrared spectrophotometer which includes a monochromator for resolving the reflected light into light of a discrete wavelength;
   (c) a database containing a reference calibration equation linking absorption characteristics by wavelength and the quantified presence of the parameter of interest; and
   (d) a computer for measuring the parameter by application of the calibration equation to the obtained spectrum for a sample and managing said system.

2. The system according to claim 1, wherein said scanning head mounting includes vibration dampening.

3. The system according to claim 1, wherein said spectrophotometer is vibration insulated.

4. The system according to claim 1, wherein said spectrophotometer is temperature insulated.

5. The system according to claim 1, wherein said spectrophotometer is contained within an insulated and air-conditioned chamber.

6. The system according to claim 1, wherein said sensing head is remote from said spectrophotometer and is linked thereto by a fiber optic cable.

7. The system according to claim 1, wherein said database comprises a plurality of reference calibration equations.

8. The system according to claim 1, wherein said scanning head is mounted adjacent a feed chute for crushing rollers.

9. A network comprising a plurality of systems according to claim 1, said spectrophotometers of said network being standardised to one spectrophotometer within said network which serves as a master spectrophotometer.

10. A method of on-line measurement of a parameter in processed sugar cane, the method comprising the steps of:
   (i) obtaining an infrared reflectance spectrum from a stream of said processed cane;
   (ii) applying an appropriate calibration equation to the spectrum to quantify the presence of the parameter of interest; and
   (iii) statistically validating the spectrum obtained as being represented by the calibration equation.

11. The method according to claim 10, wherein said parameter is selected from fiber content, juice brix, juice polarisation, commercial cane sugar, quality parameters, inorganic elements, or process parameters.

12. The method according to claim 10, wherein said processed sugar cane is selected from prepared cane, intermediate and final crushing roller bagasse, boiler feed materials, raw sugar, or crystalline sugar.

13. The method according to claim 10, wherein said spectrum is a single spectrum or the average of a plurality of obtained spectra.

14. The method according to claim 10, wherein said spectrum is measured over the range of 400 to 2,500 nm.

15. The method according to claim 10, wherein said infrared reflectance spectrum is obtained from a portion of the processed sugar cane passing through a by-pass line.

16. The method according to claim 10, wherein said infrared reflectance spectrum is obtained from a stream set up for analytical purposes.

* * * * *